United States Patent
Ogawa (10) Patent No.: US 8,199,403 B2
(45) Date of Patent: Jun. 12, 2012

(54) LIGHT POLARIZATION CONTROL USING SERIAL COMBINATION OF SURFACE-SEGMENTED HALF WAVELENGTH PLATES

(75) Inventor: Riki Ogawa, Kanagawa (JP)

(73) Assignees: Kabushiki Kaisha Toshiba, Tokyo (JP); NEC Corporation, Tokyo (JP)

( * ) Notice: Subject to any disclaimer, the term of this patent is extended or adjusted under 35 U.S.C. 154(b) by 550 days.

(21) Appl. No.: 12/404,569

(22) Filed: Mar. 16, 2009

(65) Prior Publication Data

US 2009/0237909 A1    Sep. 24, 2009

(30) Foreign Application Priority Data

Mar. 18, 2008    (JP) .................................. 2008-068919

(51) Int. Cl.
*G02B 27/28*    (2006.01)
(52) U.S. Cl. ..................................... 359/486.03; 362/19
(58) Field of Classification Search . 359/486.01–486.03
See application file for complete search history.

(56) References Cited

U.S. PATENT DOCUMENTS

| | | | |
|---|---|---|---|
| 3,941,476 A | * | 3/1976 | Stauffer .............................. 356/3 |
| 2007/0159694 A1 | * | 7/2007 | Brown et al. .................. 359/489 |
| 2009/0316263 A1 | * | 12/2009 | Gerton et al. ................. 359/489 |

FOREIGN PATENT DOCUMENTS

JP    2007-193025    8/2007

* cited by examiner

*Primary Examiner* — Lee Fineman
(74) *Attorney, Agent, or Firm* — Oblon, Spivak, McClelland, Maier & Neustadt, L.L.P.

(57) ABSTRACT

A light polarization control apparatus includes a linear polarized light generation device for generating a linearly polarized light ray; and a pair of first and second four-division type half-wave plate located at front and back positions of a light axis, each said half-wave plate having a surface divided into four regions by a couple of boundary lines crossing together at right angles, wherein the linearly polarized light ray is guided to pass through said pair of first and second four-division type half-wave plate to thereby divide this light ray into eight areas each having its polarization state as converted to any one of a azimuthally polarized state and a radially polarized state.

20 Claims, 10 Drawing Sheets

LIGHT POLARIZATION CONTROL USING SERIAL COMBINATION OF SURFACE-SEGMENTED HALF WAVELENGTH PLATES

CROSS-REFERENCE TO RELATED APPLICATION(S)

Priority is claimed to Japanese Patent Application No. 2008-068919, filed Mar. 18, 2008, the disclosure of which is incorporated herein by reference.

FIELD OF THE INVENTION

The present invention relates generally to light polarization technologies and, more particularly, to a method and apparatus for controlling the polarization state of an illumination light ray for use in highly integrated semiconductor lithography tools and ultra-fine pattern inspection systems.

DESCRIPTION OF RELATED ART

In currently available semiconductor microlithography apparatus and workpiece inspection systems, it is well known that the image resolution is improvable by controlling the polarization of an illumination light beam to go into a radially polarized state or a azimuthally polarized state. One convenient approach to doing this is to use a surface-segmented wavelength plate which is placed within an illumination light system for controlling the polarization direction of an incident light ray on a per-region basis.

Typical examples of the surface-segmented wavelength plate are four-division type wavelength plates and eight-division type wavelength plates, as disclosed in Published Unexamined Japanese Patent Application No. JP 2007-193025A. An advantage of this design lies in an ability to create a multi-segmented radially or azimuthally polarized state of illumination light, which becomes closer to the ideal with an increase in number of segmented regions of the wave plate. Unfortunately, this advantage does not come without accompanying penalties which follow: an increase in manufacturing cost and a decrease in system performance. These are due to an increase in machining accuracy required to fabricate such multi-segmented wavelength plate.

SUMMARY OF THE INVENTION

It is therefore an object of this invention to provide a technique capable of independently controlling the polarization states of an increased number of areas within a beam of light without having to excessively increase the division number of a surface-segmented wavelength plate.

Another object of the invention is to provide a technique capable of independently controlling the polarized state of each of many areas within a light beam while at the same time avoiding unwanted cost increase and performance deterioration.

To attain the foregoing objects, in accordance with one aspect of this invention, a light polarization control apparatus is provided which is arranged to include a light source device for generating a linearly polarized light ray, and a pair of four-division type half-wave plate which are located at front and back positions of a light axis. Each half-wave plate has a surface divided into four regions by two boundary lines crossing together at right angles. The linearly polarized light is guided to pass through the pair of four-divided half-wave plates to thereby divide this light into eight areas. Each area has its polarization state that is convertable to a radially or azimuthally polarized state.

In accordance with another aspect of the invention, a light polarization control apparatus is provided, which includes a light source for generating a linearly polarized light ray, and a pair of two-division type half-wave plates which are located at front and back positions of a light axis. Each half-wave plate has a surface that is divided into two regions by a boundary line. The linearly polarized light ray passes through the pair of two-divided half-wave plates so that this ray is divided into four areas, each of which has its polarization state that is convertable to a radially or azimuthally polarized state.

In accordance with a further aspect of the invention, a light polarization control method is provided, which includes the steps of placing along a light axis a pair of four-division type half-wave plate each having a surface divided into four regions by a couple of boundary lines crossing together at right angles, guiding a linearly polarized light ray to pass through the pair of four-divided half-wave plates to thereby divide the polarization state of an outgoing light ray into eight areas, and changing the polarization state of each area to either a radially polarized state or a azimuthally polarized state.

In accordance with another further aspect of the invention, a light polarization control method includes the steps of placing along a light axis a pair of two-division type half-wave plates each having a surface divided into two regions by a boundary line, guiding a linearly polarized light ray to pass through the pair of two-divided half-wave plates to thereby divide the polarized state of outgoing light into four different areas, and changing the polarized state of each area to a radially polarized or azimuthally polarized state.

According to one of these aspects of the invention, it is possible to independently control the polarized state of each of many areas within a light beam without excessively increasing the division number of each division type half-wave plate.

Another advantage of one of these aspects of the invention lies in the ability to provide the technique for enabling independent control of the polarized state of each of many areas within the light beam while at the same time avoiding unwanted cost increase and performance degradation.

BRIEF DESCRIPTION OF THE DRAWINGS

FIGS. 3 and 4 are diagrams each showing a configuration of a light polarization control apparatus in accordance with one embodiment of this invention, which has a pair of spaced-apart four-division type $\lambda/2$ plates along the light axis of a linear polarized light emitting light source, wherein FIG. 3 is for production of an eight-direction radial polarized light beam whereas FIG. 4 is for production of an eight-division circumferential polarized light.

FIGS. 6 and 7 are diagrams each showing a light polarization control apparatus in accordance with another embodiment of the invention, which includes a pair of two-segmented λ/2 plates along the light axis of a linear polarized light emitter, wherein FIG. 6 is for production of an four-direction radial polarized light beam whereas FIG. 7 is for production of an four-division circumferential polarized light.

DETAILED DESCRIPTION OF THE INVENTION

Currently preferred embodiments of light polarization control apparatus and methodology incorporating the principles of this invention will be described in detail with reference to the accompanying figures of the drawing below.

Figure 1:
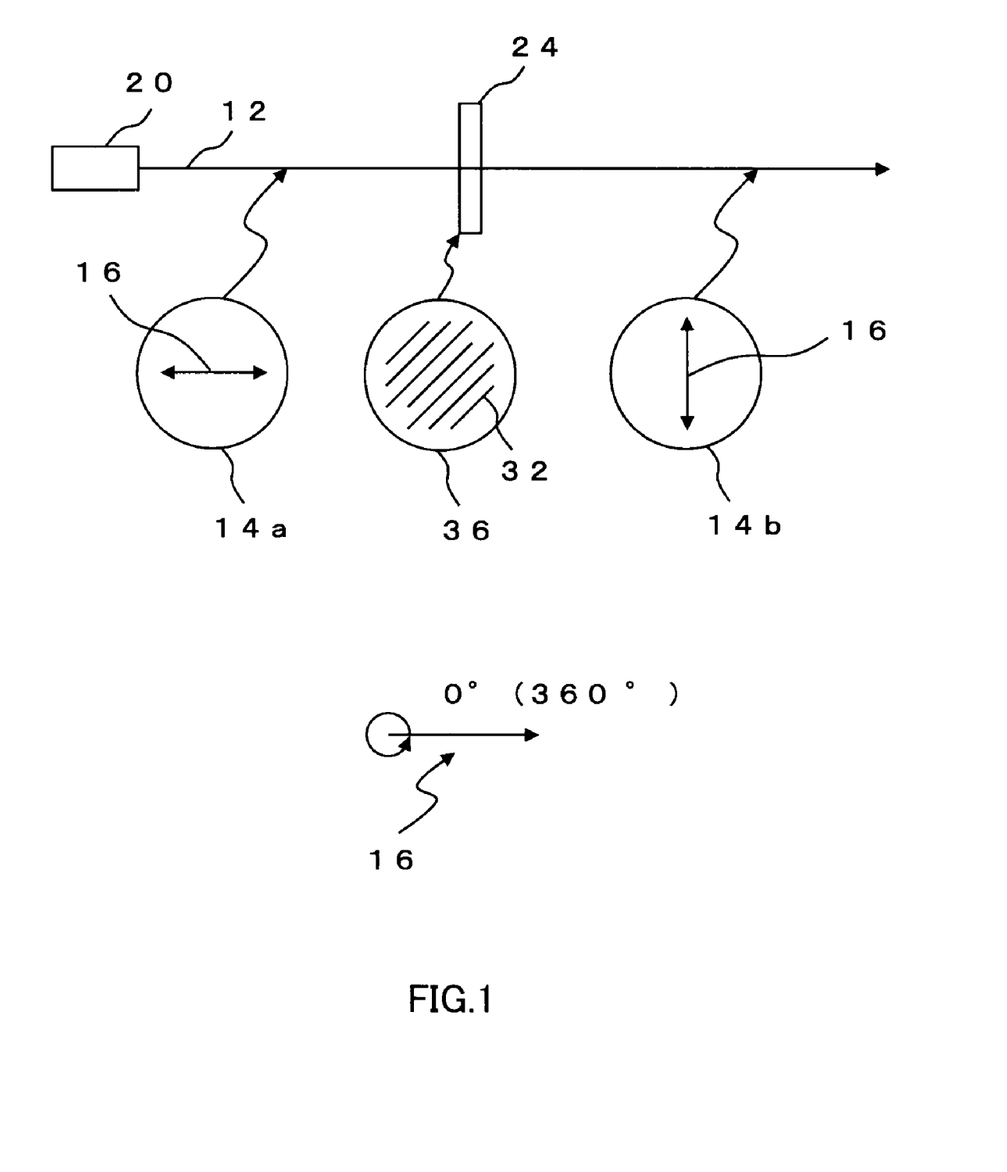
FIG. 1 is a diagram showing a pictorial representation of a configuration for light polarization control which includes a linear polarized light emission device and its associated half wavelength ($\lambda/2$) plate, for explanation of optical characteristics of the $\lambda/2$ plate.

Referring to FIG. 1, a basic configuration of a light polarization control apparatus is shown. This apparatus includes a light source 20—here, a linearly polarized light emitting device—and a half wavelength (λ/2) plate 24 (half-wave plate) associated therewith. This diagram pictorially shows the direction of an optical axis 32 of the λ/2 plate 24 and the rotation of a polarization direction 16 within luminous fluxes of incoming and outgoing light beams of the λ/2 plate 24. The optical axis 32 of λ/2 plate 24 is indicated to be set in an optical axis state 36. The polarization direction 16 is shown in a polarized state 14.

In the optical structure shown in FIG. 1, the light source 20 produces a beam of linearly polarized light. This beam travels along a light axis 12 (propagation direction of light) while having its polarization direction 16 as set in a zero-degree linear polarized state 14a. When this light beam passes through the λ/2 plate 24, the beam polarization direction 16 is rotated by an angle of ninety (90) degrees so that this light is changed in polarization to have a 90-degree linearly polarized state 14b, which is altered from the 0-degree polarized state 14a. Note here that in every figure of the drawing, the polarized state 14a or 14b indicates the polarizing direction of light when looking at from the light axis 12; similarly, the optical axis state 36 indicates the direction of optical axis 32 when viewing from the light axis 12.

When the linearly polarized beam that emerged from the light source 20 is incident upon the λ/2 plate 24, the polarization direction 16 of an outgoing ray of plate 24 is rotated by an angle of 2θ, where θ is the angle between the polarization direction 16 of incoming light and the optical axis 32 of λ/2 plate 24. This angle θ is 45 degrees in FIG. 1; so, the polarization direction 16 of the output light is equal to 90 degrees. This means that the polarization direction 16 of output light of λ/2 plate 24 is rotated by 90 degrees with respect to the polarization direction 16 of the incident light of plate 24. Note that the angle of zero (or 360) degrees of the light polarization direction 16 is defined by the horizontal angle, i.e., the direction of a horizontal plane containing the light axis 12 as shown at lower part of FIG. 1.

Figure 2:
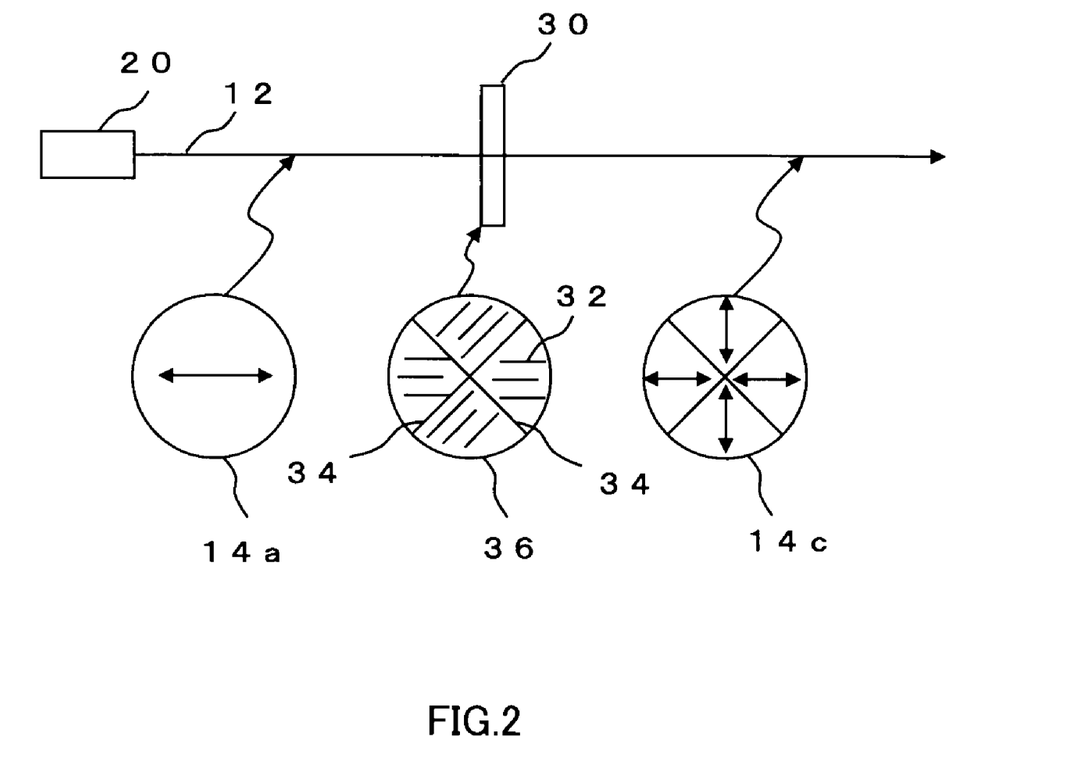
FIG. 2 is a pictorial representation of a configuration for polarization control with the $\lambda/2$ plate of FIG. 1 being replaced by a four-division type $\lambda/2$ plate.

Referring next to FIG. 2, another light polarization control apparatus is shown, which is similar to that shown in FIG. 1 with the λ/2 plate 24 being replaced by a four-division type λ/2 plate 30. This plate is the one that has its light-receiving surface or "phase-shift plane" being divided or segmented into four equal-size areas. When the light source 20 emits a linearly polarized light beam of the zero-degree polarized state 14a, this beam is incident upon the four-divided λ/2 plate 30 (four-divided half-wave plate). When passing through this plate, the incident light is converted into a light beam having a radially polarized state 14c, which consists of four fan-shaped areas. The four-divided λ/2 plate 30 is made up of a plurality of—here, four—λ/2 plate segments which are combined together in such a manner that a couple of boundary lines 34 cross together at right angles at the center of a circle corresponding to an outer shape of this plate 30. Each half-wave plate segment has its optical axis 32 that is set in an optical axis state 36 as shown in FIG. 2. This optical axis state 36 is one example, and similar results are obtainable by rotating the optical axis 32 by a specific angle which is n times greater than 90 degrees, where "n" is a positive integer.

In the manufacture of such surface-divided λ/2 plate 30, it is required to precisely bond together respective plate segments or regions without any space gap between two adjacent ones of them. This is because the presence of a gap therebetween would result in unwanted production of scattered light, which gives rise to illumination irregularities and/or loss of effective light fluxes. To avoid this, a need is felt to perform high-precision machining in a way such that the angle of boundary lines crossing together at the center of a round disc-like wavelength plate, i.e., radial center point, becomes exactly equal to 90 degrees for four-divided half-wave plates or 45 degrees for eight-divided half-wave plates. As the 30) plate-surface segmentation number increases, accumulation of position alignment errors increases accordingly. This results in an impermissibly excessive increase in machining accuracy required. Thus it is desirable to set the surface division number of λ/2 plate at a least possible number.

Embodiment 1

Figure 3:
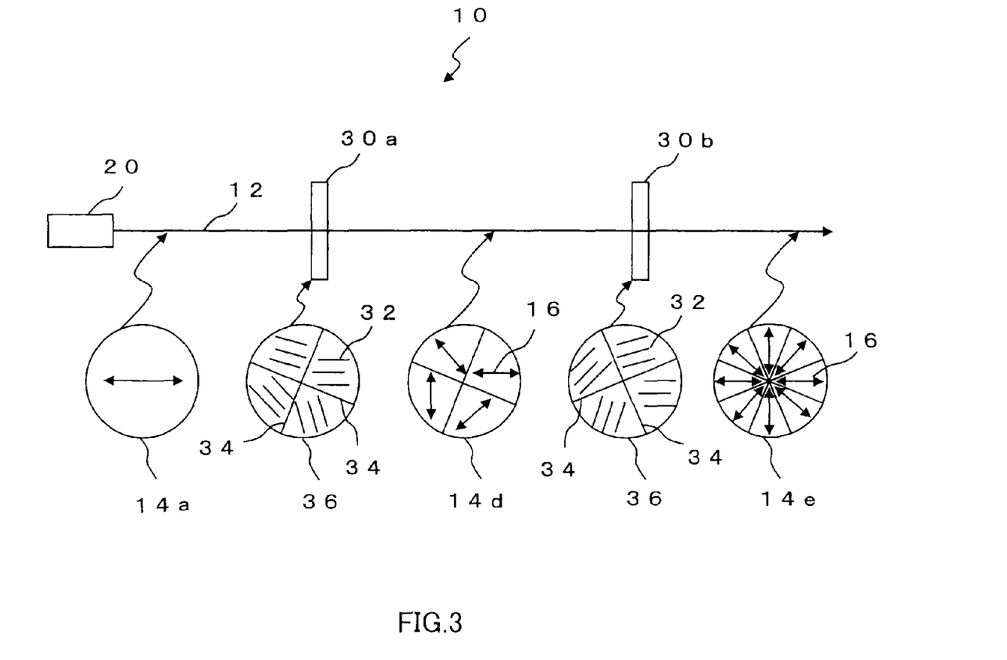

Turning to FIG. 3, a light polarization control apparatus 10 in accordance with an embodiment of this invention is shown. The light polarization controller 10 includes a light source 20, which is constituted from a linearly polarized light emitting device 20 similar to that shown in FIGS. 1 and 2. The polarization controller 10 also includes a pair of spaced-apart half wavelength (λ/2) plates 30a and 30b. Each λ/2 plate 30a, 30b is of a round disc-like shape and has its incident light reception surface with a phase-shift plane which is segmented into a less number of equal-size fan-like areas—here, four areas. The linearly polarized light emitter 20 and four-divided λ/2 plates 30a-30b are aligned together along the principal axis 12 of a light beam emitted. Examples of the linear polarized light emitter 20 include, but not limited to, a gas laser device and a solid-state laser device, such as a semiconductor laser. In the illustrative embodiment, by locating the couple of spaced-apart surface-segmented λ/2 plates 30a-30b along the light axis 12, the resulting number of light flux areas increases. This in turn causes a polarizer module made up of these two wave plates 30a-b to increase in plate-surface segmentation number as a whole.

In the polarization controller 10, the light source 20 emits at its output a linearly polarized light beam, which is set in a polarized state 14a having its angle being set at zero (0) degrees relative to the light axis 12. This linear polarized light travels along the light axis 12. When this light is incident upon and passes through the four-segmented λ/2 plate 30a at the front stage, its output light is set in a four-division polarized state 14d. In this state the beam's profile is divided into four fan-shaped areas, adjacent ones of which are different from each other in polarization direction as shown in FIG. 3. This four-division polarized light progresses along the light axis 12 to hit the next four-segmented λ/2 plate 30b at the rear stage. When this light passes through the rear-stage λ/2 plate 30b, its output light beam goes into an eight-direction radially polarized state 14e having eight fan-like areas. Achievement of this radial polarization is owing to the fact that the front- and rear-stage four-segmented λ/2 plate 30a and 30b are different from each other in optical axis state 36. More precisely, these plates are different from each other in directions of surface-segmentation boundary lines 34 and optical axes 32 of respective segmented regions as shown in FIG. 3.

Very importantly, the division of the light profile into eight radially polarized flux areas is owing to the use of the pair of spaced-apart four-segmented λ/2 plate 30a and 30b, which are specifically arranged so that a cross-shape pattern that is formed of the perpendicularly crossed boundary lines 34 of front-stage λ/2 plate 30a is angularly offset by forty five (45) degrees from that of the rear-stage λ/2 plate 30b as shown in FIG. 3. Thus the optical axis 32 of one segmented region of plate 30a is rotated by 45 degrees from that of a corresponding region of plate 30b. This rotation angle setup of optical axis 32 is one example. Similar results are obtainable by increasing or reducing the offset angle of the optical axis 32 by a prespecified angle which is n times greater than 90 degrees, where "n" is a positive integer.

Figure 4:
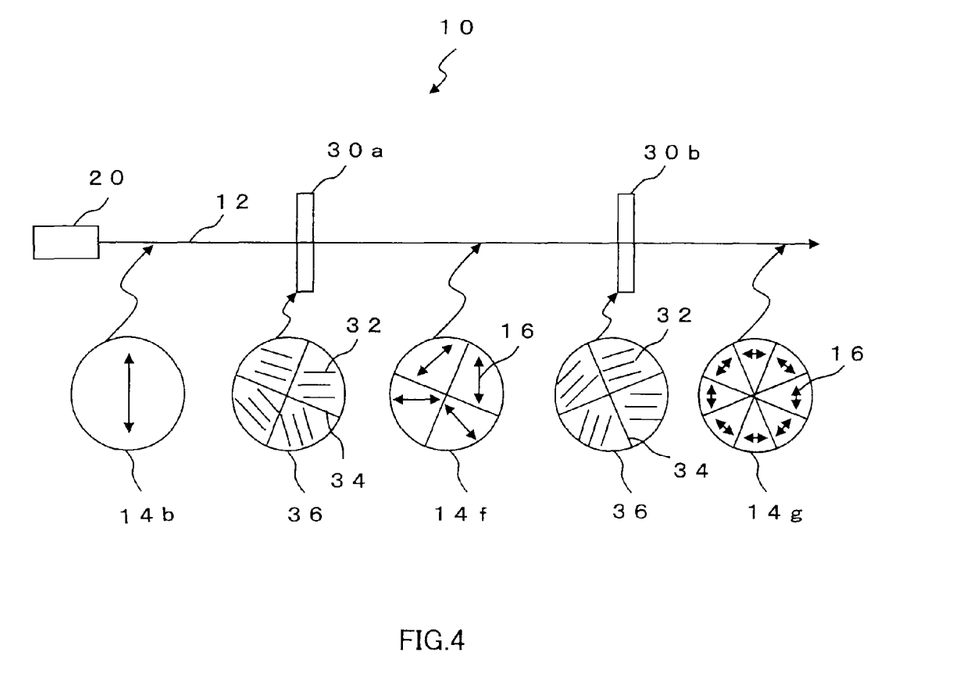

A modified configuration of the light polarization control apparatus 10 is shown in FIG. 4. This apparatus is similar to that shown in FIG. 3 except that the light source 20 is arranged to emit a linearly polarized light beam which is set in a polarized state 14b with its polarization direction of ninety (90) degrees. This 90-degree linear polarized light beam travels along the light axis 12 to hit the front-stage four-segmented λ/2 plate 30a. When the incident light passes through this plate, its output light is set in a four-division polarized state 14f. Thereafter, when this light passes through the rear-stage four-segment λ/2 plate 30b, its output light is set in an eight-division azimuthally polarized state 14g with eight fan-shaped areas as shown in FIG. 4. The polarization directions of each of the above-stated polarized states 14e and 14g are determinable through computation by using a set of mathematical formulas as will be presented later.

Figure 5:
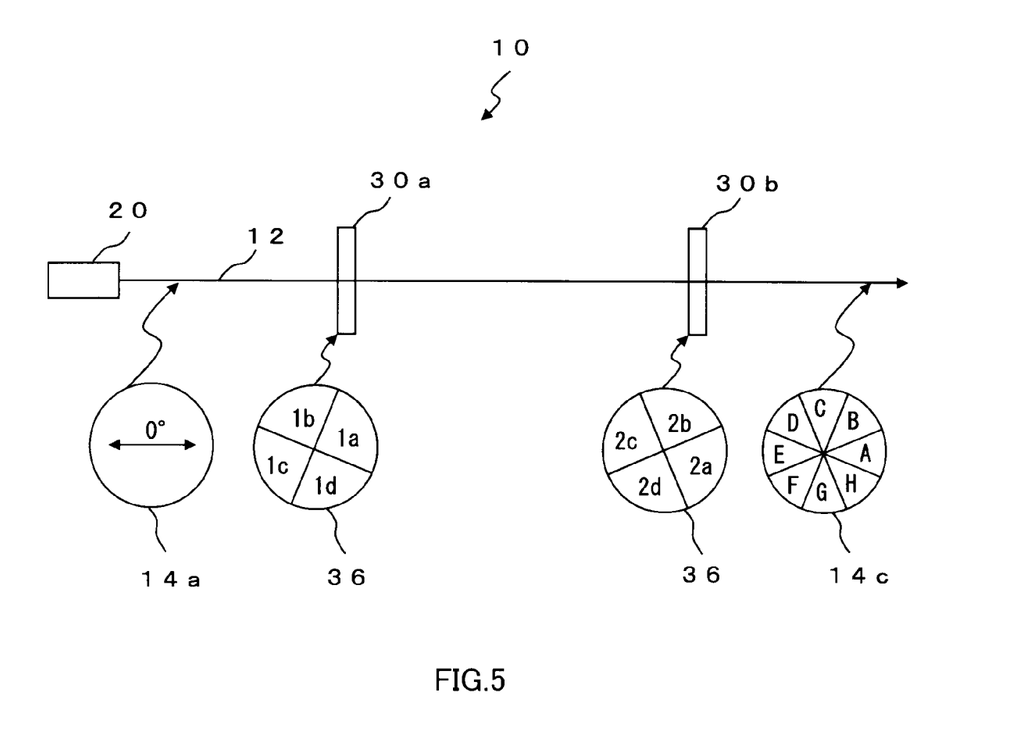
FIG. 5 is a diagram for explanation of a process of calculating polarization states in eight directions.

Quantitative analysis will now be given of the light polarization to be performed by the embodiment controller 10 of FIG. 3 with reference to FIG. 5 below. Let the polarization direction of an incident light ray be zero (0) degrees. Let the directions of optical axes 32 of phase-sift regions 1a, 1b, 1c and 1d of the front-stage four-segmented λ/2 plate 30a be $\phi_{1a}$, $\phi_{1b}$, $\phi_{1c}$ and $\phi_{1d}$, respectively. Similarly, let the directions of optical axes 32 of regions 2a to 2d of the rear-stage four-segment λ/2 plate 30b be $\phi_{2a}$ to $\phi_{2d}$, respectively. After having passed through these wave plates 30a-30b, the resultant light beam changes in polarized state and thus has an eight-division polarized state 14h, in which a cross-section or "profile" of the beam is divided into eight fan-shaped areas A to H as shown in FIG. 5. Each of these areas is settable in a desired polarization direction in a way independent of the other areas. In the polarized state 14h, these eight areas A to H have their own polarization directions $\theta_A$ to $\theta_H$, respectively. Accordingly, in the case of obtaining the radially polarized state such as shown in FIG. 3, the polarization directions $\theta_A$ to $\theta_H$ are given by Equations (1) to (8) which follow:

$$\theta_A=\phi_{2a}-(2\phi_{1d}-\phi_{2a})=2\phi_{2a}-2\phi_{1a}=0+180n_A, \quad (1)$$

$$\theta_B=2\phi_{2b}-2\phi_{1a}=45+180n_B, \quad (2)$$

$$\theta_C=2\phi_{2b}-2\phi_{1b}=90+180n_C, \quad (3)$$

$$\theta_D=2\phi_{2c}-2\phi_{1b}=45+180n_D, \quad (4)$$

$$\theta_E=2\phi_{2c}-2\phi_{1c}=0+180n_E, \quad (5)$$

$$\theta_F=2\phi_{2d}-2\phi_{1c}=45+180n_F, \quad (6)$$

$$\theta_G=2\phi_{2d}-2\phi_{1d}=90+180n_G, \quad (7)$$

$$\theta_H=2\phi_{2a}-2\phi_{1d}=45+180n_H, \quad (8)$$

where $n_A$ to $n_H$ are given integers.

From the set of Equations (1) to (8), we obtain the following relations represented by a second set of Equations (9) to (12) with respect to the front-stage four-segmented λ/2 plate 30a:

$$\phi_{1b}-\phi_{1a}=-22.5-90(n_C-n_B), \quad (9)$$

$$\phi_{1c}-\phi_{1b}=-22.5-90(n_E-n_D), \quad (10)$$

$$\phi_{1d}-\phi_{1c}=-22.5-90(n_G-n_F), \quad (11)$$

$$\phi_{1a}-\phi_{1d}=-22.5-90(n_A-n_H). \quad (12)$$

Therefore, letting $\phi_{1a}=0+90n_{1a}$, the angles of optical axes of respective regions 1a-1d are represented by a third set of Equations (13)-(16) below:

$$\phi_{1a}=0+90n_{1a}, \quad (13)$$

$$\phi_{1b}=-22.5+90n_{1b}, \quad (14)$$

$$\phi_{1c}=-45+90n_{1c}, \quad (15)$$

$$\phi_{1d}=-67.5+90n_{1d}, \quad (16)$$

where $n_{1a}$ to $n_{1d}$ are given integers.

Similarly, while letting $\phi_{2a}=0+90n_{2a}$ for the rear-stage four-segment λ/2 plate 30b, we obtain the following relations of a fourth set of Equations (17) to (20):

$$\phi_{2a}=0+90n_{2a}, \quad (17)$$

$$\phi_{2b}=22.5+90n_{2b}, \quad (18)$$

$$\phi_{2c}=45+90n_{2c}, \quad (19)$$

$$\phi_{2d}=67.5+90n_{2d}, \quad (20)$$

where $n_{2a}$ to $n_{2d}$ are given integers.

From the foregoing, the optical axis setup conditions of the paired four-segment λ/2 plates 30a-30b are quantitatively definable. By setting all of the values $n_{1a}-n_{1d}$ and $n_{2a}-n_{2d}$ at 0, the embodiment for eight-division radial polarization shown in FIG. 3 is achieved.

On the contrary, when 90-degree linear polarized light is used in place of the zero-degree polarized light to pass through the pair of four-segmented λ/2 plates 30a and 30b as in the apparatus shown in FIG. 4, the eight-division azimuthally polarized state 14g is obtainable. This is apparent from the first set of Equations (1)-(8). Setting the incident light's linear polarized state at 90 degrees is equivalent to a mathematical operation of adding a value "90" to the left-hand side term in each of Equations (1)-(8). Creating the azimuthally polarized state is representable by addition of "90" to the right-hand side term. Accordingly, these are cancelled out each other, resulting in establishment of mathematical formulas that are identically the same as Equations (1)-(8).

Embodiment 2

Figure 6:
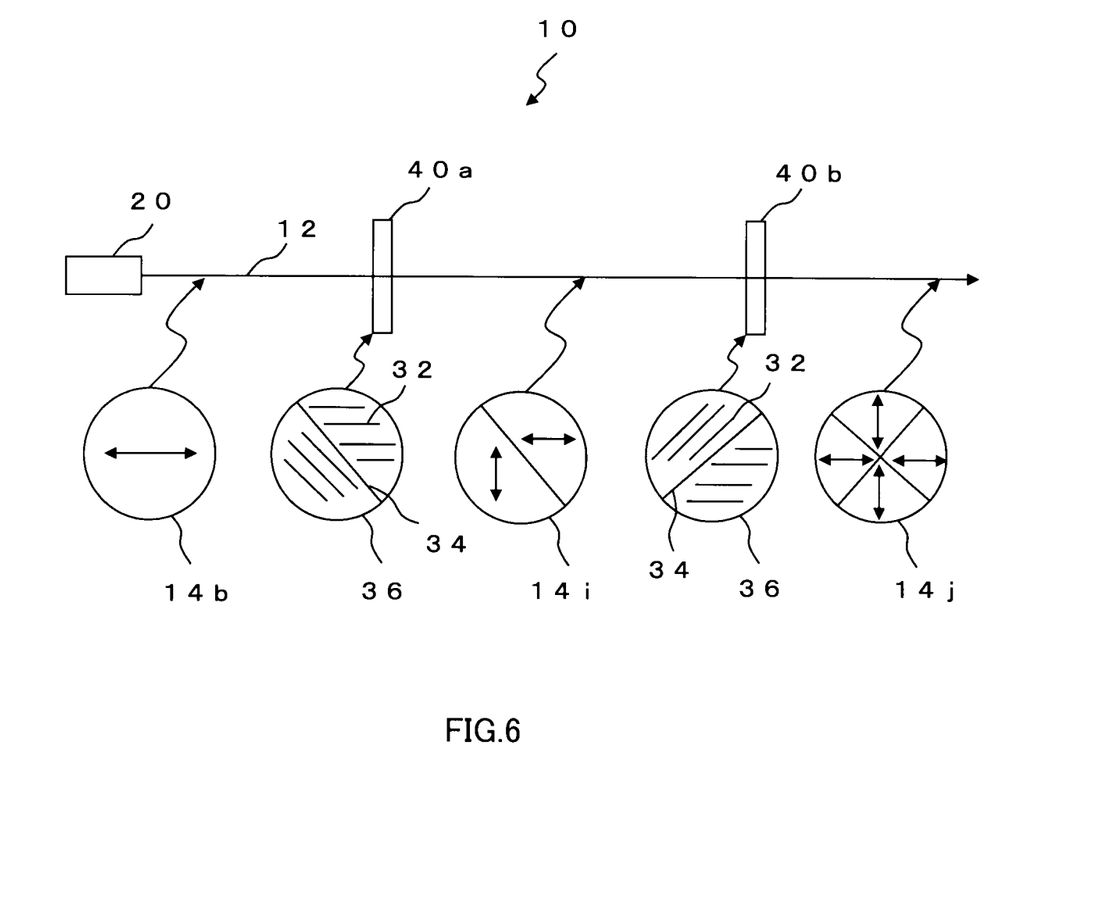

A light polarization control apparatus 10 in accordance with another embodiment of this invention is shown in FIG. 6. This embodiment controller is arranged to employ a couple of spaced-apart two-segmented type λ/2 plates 40a and 40b, rather than the four-segmented λ/2 plates 30a-30b shown in FIG. 3 or 4. By using these two-segment λ/2 plates 40a-40b, the polarization controller 10 creates a four-direction radially polarized state 14j having four fan-like areas as shown in FIG. 6.

More specifically, the light source 20 emits at its output a linearly polarized light beam, which is set in the polarized state 14a with its polarization angle of 0 degrees. This zero-degree linear polarized light travels along the principal axis 12. When this light passes through the two-segmented λ/2 plate 40a at the front stage, it changes in polarization to have a polarized state 14i. When this light penetrates the next two-segmented λ/2 plate 40b in the rear stage, its output light is set in a radially polarized state 14j having four equal-size fan-shaped areas. To generate this four-direction radial polarized state 14j, the paired two-segment λ/2 plates 40a and 40b are arranged so that a surface segmentation boundary line 34 of the front-stage λ/2 plate 40a (half-wave plate) is offset by an angle of 90 degrees from that of the rear-state λ/2 plate 40b (half-wave plate). Thus the optical axis 32 of one segmented region of the plate 40a is rotated by 90 degrees from that of its corresponding region of the plate 40b. This angle offset of the optical axis 32 is exemplary only, and similar results are still obtainable by increasing or reducing the direction of optical axis 32 by a constant angle which is an integral multiple of 90 degrees.

Figure 7:
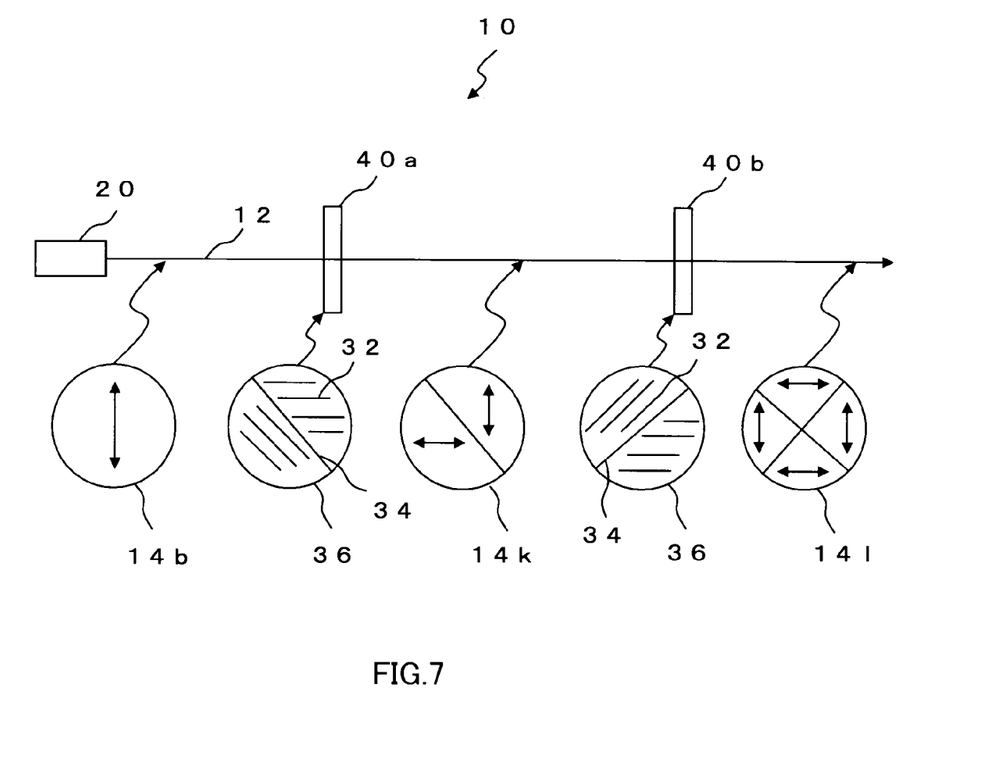

The polarization controller 10 of FIG. 6 is modifiable as shown in FIG. 7, wherein the light source 20 is arranged to emit a linearly polarized light beam which is set in a polarized state 14b with its polarization angle of 90 degrees, rather than the zero-degree linear polarized state 14a. The 90-degree linear polarized light beam travels along the light axis 12. When this light enters and passes through the front-stage two-segmented λ/2 plate 40a, its output light has a polarized state 14k. When this light passes through the next, rear-stage two-segment λ/2 plate 40b, its output light is set in a four-division azimuthally polarized state 14l having four equal-size fan-shaped areas. The directions of optical axes 32 shown in FIG. 7 are calculable using a fifth set of mathematical formulas to be presented later.

Quantitative analysis will now be given of the light polarization of the apparatus 10 of FIG. 6 with reference to FIG. 8 below. Let the polarization direction of incoming light be zero (0) degrees. Let the directions of optical axes 32 of respective regions 1a and 1b of the front-stage two-segmented λ/2 plate 40a be $\phi_{1a}$ and $\phi_{1b}$, respectively. Similarly, let the directions of optical axes 32 of regions 2a and 2b of the rear-stage two-segment λ/2 plate 40b be $\phi_{2a}$ and $\phi_{2b}$, respectively.

Figure 8:
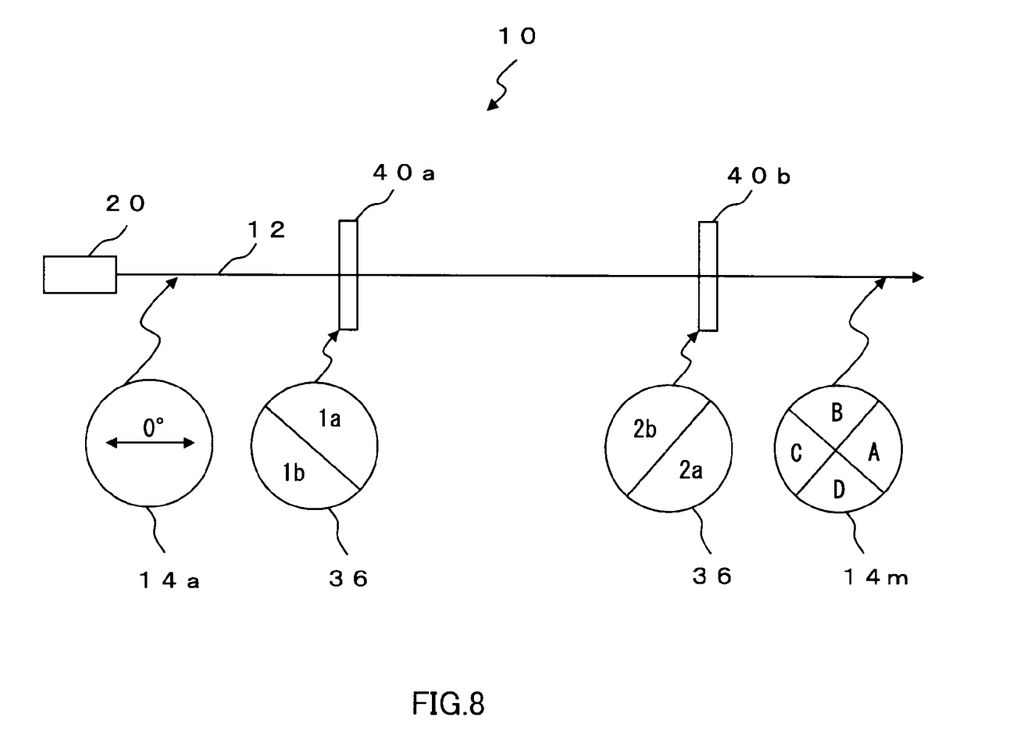
FIG. 8 is a diagram for explanation a process of calculating polarized states in four directions.

After having passed through these plates 40a-40b, the resultant light changes in polarization state and thus has a polarized state 14m shown in FIG. 8, which consists of four equally divided or "quadrisected" areas A to D. Each of these areas is settable in a desired polarization direction in a way independent of the others. In the four-division polarized state 14m, these four areas A to D have their own polarization directions $\theta_A$ to $\theta_D$, respectively. The front-stage wave plate 40a has different optical axis angles $\phi_{1a}$ to $\phi_{1b}$ in its respective bisected regions 1a and 1b; the rear-stage plate 40b has optical axis angles $\phi_{2a}$ to $\phi_{2b}$ in bisected regions 2a and 2b, respectively. Through calculation similar in principle to that in the case of eight-division polarization shown in FIG. 5, these angles $\phi_{1a}$ to $\phi_{2b}$ are given as the fifth set of Equations (21) to (24) below:

$$\phi_{1a} = 0 + 90 n_{1a}, \quad (21)$$

$$\phi_{1b} = -45 + 90 n_{1b}, \quad (22)$$

$$\phi_{2a} = 0 + 90 n_{2a}, \quad (23)$$

$$\phi_{2b} = -45 + 90 n_{2b}, \quad (24)$$

where $n_{1a}$, $n_{1b}$, $n_{2a}$ and $n_{2b}$ are given integers.

From the foregoing, the optical axis direction setup conditions of the pair of two-segmented or "bisected" λ/2 plates 40a and 40b are quantitatively determinable. By setting all the values $n_{1a} - n_{1b}$ and $n_{2a} - n_{2b}$ at 0, the four-division radial polarization shown in FIG. 6 is achieved.

On the contrary, when the 90-degree linear polarized light is introduced into the pair of bisected λ/2 plate 40a-40b, the four-division azimuthally polarized state 14l of FIG. 7 is obtainable. This can be said for the same reason as that in the case of the paired four-segmented or "quadrisected" λ/2 plate 30a-b shown in FIG. 4.

Embodiment 3

Figure 9:
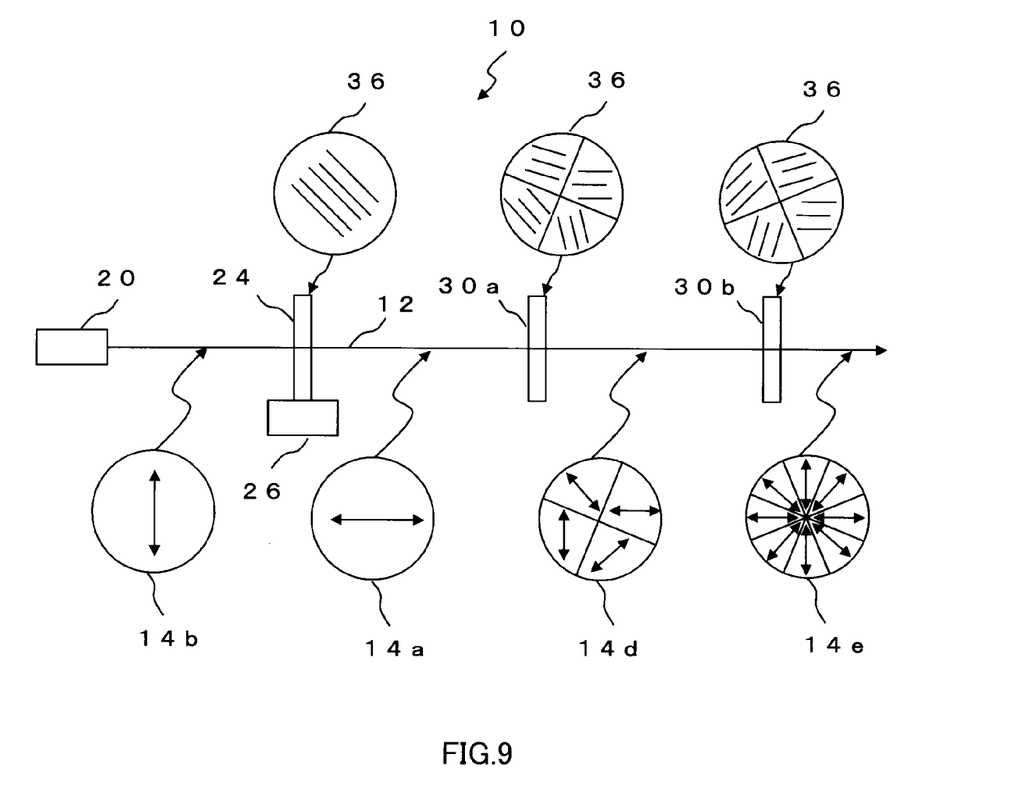
FIG. 9 shows a light polarization control apparatus in accordance with a further embodiment of the invention, which is similar to that shown FIG. 3 with a rotatable λ/2 plate being added for altering the linear polarization direction of output light of the light source.

A light polarization control apparatus 10 in accordance with a further embodiment of this invention is shown in FIG. 9. This embodiment polarization controller is similar to that shown in FIG. 3, with a rotatable disc-like half wavelength (λ/2) plate 24 being additionally provided. This rotatable wave plate 24 is of the non-segmentation type and is situated in the light axis 12 at a position midway between the light source 20 and the front-stage four-segmented or "quadrisected" λ/2 plate 30a. The additional λ/2 plate 24 has its center, which is identical to the light axis 12. The λ/2 plate 24 is associated with a rotation driving device 26 coupled thereto. This rotation driver 26 may typically be a rotating stage structure including an electrical motor, such as a stepper motor or pulse motor (not shown).

When the rotatable λ/2 plate 24 is driven by the driver 26 to rotate about the light axis 12, its incident light—i.e., light leaving the light source 20—is forced to change in polarization direction and thus have any desired angle of rotation. With additional use of the motor-driven rotatable λ/2 plate 24, the polarization controller 10 has its ability to switch the finally obtained eight-area divided polarization state to any one of the radially polarized state 14e shown in FIG. 3 and the azimuthally polarized state 14g of FIG. 4.

To create the eight-direction radially polarized state 14e in case the light source 20 is 90 degrees in linear polarization direction thereof, it is necessary to change it to zero degrees. To do this, the plate rotation driver 26 is rendered operative to drive and rotate the λ/2 plate 24 in a way such that its optical axis 32 has a changed direction with an angle of 45 degrees relative to a horizontal plane containing the light axis 12 as shown in FIG. 9. This results in that the linear polarized output beam of the light source 20 changes in polarized state—that is, the 90-degree polarized state 14b is altered to the 0-degree polarized state 14a. The resulting polarization angle-changed light, i.e., output light of the λ/2 plate 24 rotated, is guided to pass through the pair of spaced-apart quadrisected λ/2 plates 30a and 30b at front and rear stages sequentially in a similar way to that shown in FIG. 3. Thus, the finally polarization-controlled light obtained is in the intended eight-division radial polarized state 14e.

Alternatively, to create the eight-division circumferential polarized state 14g by use of the same light source 20 with the linear polarization direction of 90 degrees, the above-stated rotation driving of the rotatable λ/2 plate 24 at the first stage is not needed. In this case, the output beam of light source 20 having the 90-degree linear polarized state 14b may be guided to directly hit the front-stage quadrisected λ/2 plate 30a as in the embodiment shown in FIG. 4. Accordingly, the first-stage λ/2 plate 24 is rotated by the driver 26 so that the direction of optical axis 32 is reset at its initial angle, i.e., 90 degrees. With this angle reset operation, the light of the 90-degree linear polarized state 14b as originally emitted from the light source 20 passes through the pair of spaced-apart quadrisected λ/2 plates 30a-30b to thereby create the intended eight-division circumferential polarized state 14g in the same manner as that shown in FIG. 4.

Embodiment 4

Figure 10:
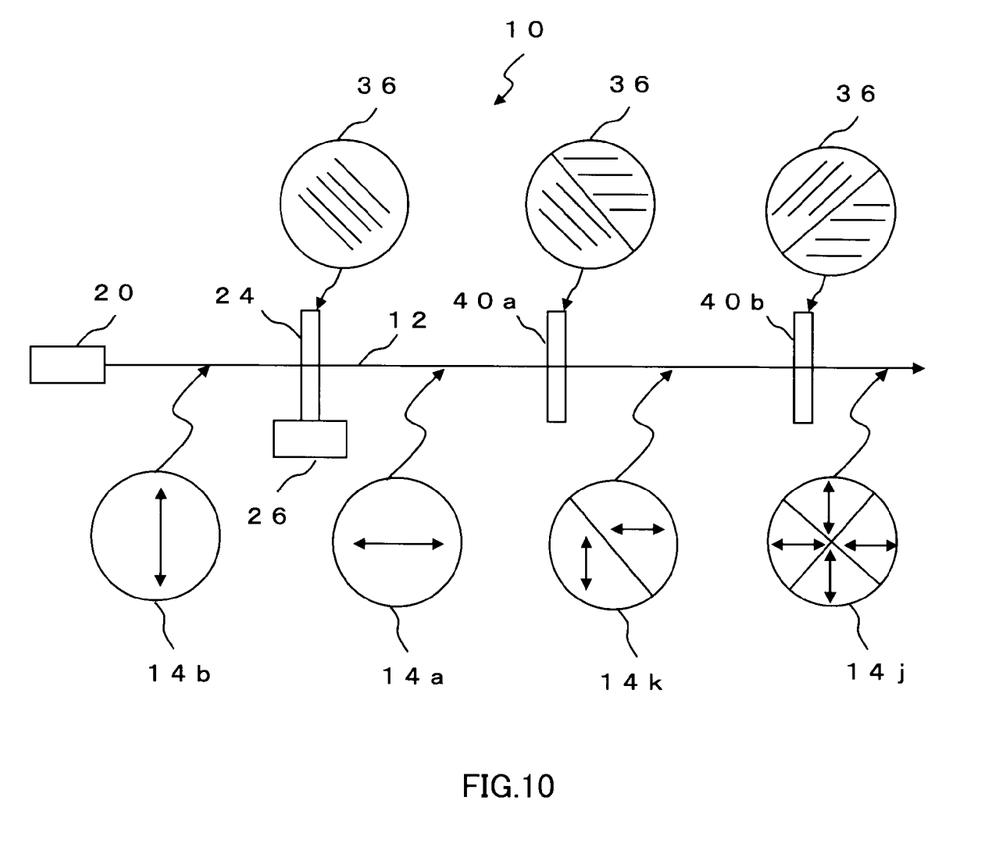
FIG. 10 shows a polarization control apparatus in accordance with another further embodiment of the invention, which is similar to that shown FIG. 6 with a rotatable λ/2 plate being added thereto.

A polarization control apparatus 10 in accordance with another further embodiment of the invention is shown in FIG. 10. This embodiment controller is similar to that shown in FIG. 6, with the rotatable non-segmentation λ/2 plate 24 of FIG. 9 being inserted into the light axis 12 at a position between the light source 20 and the front-stage bisected λ/2 plate 40a. This "first-stage" rotatable λ/2 plate 24 is driven by its associated rotation driver device 26, which is the same as that shown in FIG. 9. Additional use of the rotatable λ/2 plate 24 enables the polarization controller 10 to switch the finally obtained beam's four-division polarized state to any one of the radially polarized state 14j and the azimuthally polarized state 14l.

To create the four-division radially polarized state 14j in case the light source 20 is 90 degrees in its linear polarization direction, it is needed to change it to zero degrees. To do this, the rotation driver 26 is rendered operative to rotate the first-stage λ/2 plate 24 in a way such that its optical axis 32 is changed in direction to have a direction of 45 degrees as shown in FIG. 10. This results in the linear polarized output beam of light source 20 changing in polarization state—that is, the 90-degree polarized state 14b is changed to the zero-degree polarized state 14a in a similar way to that shown in FIG. 9. The resulting polarization angle-changed light, i.e., output light of rotatable λ/2 plate 24 that is now set in the 0-degree polarized state 14a, is guided to sequentially penetrate the pair of bisected λ/2 plates 40a and 40b at front and rear stages in a similar way to that shown in FIG. 6. Thus the intended four-division radial polarized state 14j is obtained.

To create the four-division circumferential polarized state 14l by use of the same light source 20 with the 90-degree linear polarization direction, the above-stated rotation of the rotatable λ/2 plate 24 is unnecessary. In this case the output beam of light source 20 having the 90-degree linear polarized state 14b may be guided to enter directly the front-stage bisected λ/2 plate 40a as in the embodiment shown in FIG. 7. Accordingly, the rotatable λ/2 plate 24 is rotated by the driver 26 so that the direction of optical axis 32 is reset at its initial angle, i.e., 90 degrees. With this angle resetting, the light of the 90-degree polarized state 14b as emitted from the light source 20 passes through the pair of bisected λ/2 plates 40a-b sequentially to thereby create the intended four-division circumferential polarized state 14l in the same manner as that shown in FIG. 7.

In accordance with the above-stated embodiments of this invention, the use of a pair of less-number-segmented wavelength plates 30a-30b or 40a-40b rather than a single multi-segmented wave plate makes it possible to independently control the light beam's polarized state in an increased number of divided areas therein, without having to excessively increase the surface segmentation number of the individual wave plate used. In particular, regarding the embodiments shown in FIGS. 3-4 and 9, these offer their unique advantage as to the ability to control the polarization of a light beam in at least eight different regions thereof in a way independent of one another, thereby to satisfy more successfully the requirements in polarization control for resolution improvements.

This contributes to both appreciable improvement in productivity and achievement of higher performances. In addition, when the polarization controller 10 embodying the invention is used for micro or nanoscale lithography pattern inspection of a workpiece, such as a photomask, reticle, wafer, etc., it becomes possible to increase the accuracy of such pattern inspection.

Although the invention has been disclosed and illustrated with reference to particular embodiments, the principles involved are susceptible for use in numerous other embodiments which will be apparent to persons skilled in the art. The invention is, therefore, to be limited only as indicated by the scope of the appended claims.

What is claimed is:

1. A light polarization control apparatus comprising:
   a linear polarized light generation device for generating a linearly polarized light ray; and
   a pair of first and second four-division type half-wave plates located at front and back positions of a light axis, each said half-wave plate having a surface divided into four regions by a couple of boundary lines crossing together at right angles, wherein
   the linearly polarized light ray is guided to pass through said pair of first and second four-division type half-wave plate to thereby divide this light ray into eight areas each having its polarization state as converted to any one of a azimuthally polarized state and a radially polarized state.

2. The apparatus according to claim 1, wherein an angle which is formed by one of the boundary lines of the first four-division type half-wave plate and one of the boundary lines of the second four-division type half-wave plate is substantially equal to forty five (45) degrees and wherein each angle between each extraordinary axis of the first and second four-division type half-wave plates and a polarization direction of incident light is any one of −67.5, −45, −22.5, 0, +22.5, +45, +67.5 and +90 degrees.

3. The apparatus according to claim 1, wherein said linear polarized light generation device is equipped with a third half-wave plate having a rotation mechanism and wherein the polarization state of outgoing light from said pair of first and second half-wave plates is switched to any one of the radially polarized state and the azimuthally polarized state by changing a rotation angle of said third half-wave plate having said rotation mechanism.

4. A light polarization control apparatus comprising:
   a linear polarized light generation device for generating a linearly polarized light ray; and
   a pair of first and second two-division type half-wave plates located at front and back positions of a light axis, each said half-wave plate having a surface divided into two regions by a boundary line, wherein
   the linearly polarized light ray is guided to pass through said pair of first and second two-division type half-wave plates to thereby divide this ray into four areas each having its polarization state as converted to any one of a azimuthally polarized state and a radially polarized state.

5. The apparatus according to claim 4, wherein an angle which is formed by one of the boundary lines of the first two-division type half-wave plate and one of the boundary lines of the second two-division type half-wave plate is substantially equal to ninety (90) degrees and wherein each angle between each extraordinary axis of any region of the first and second two-division type half-wave plates and a polarization direction of incident light is
   any one of −45, 0, +45 and +90 degrees.

6. The apparatus according to claim 4, wherein said linear polarized light generation device is equipped with a third half-wave plate having a rotation mechanism and wherein the polarization state of outgoing light from said pair of first and second half-wave plates is switched to any one of the radially polarized state and the azimuthally polarized state by changing a rotation angle of said third half-wave plate having said rotation mechanism.

7. An apparatus for producing a multi-segmentally polarized light beam having rays differing in polarization state, comprising:
   a light source having an output for emission of a beam of linearly polarized light traveling along a principal axis;
   a first polarizing plate being situated in the principal axis of the light to oppose the output of said light source and having a surface segmented into a plurality of first regions of substantially equal size including adjacent ones being different in polarization direction from each other; and
   a second polarizing plate coaxially spaced apart from the first plate along the light axis, the second plate having its surface segmented into a plurality of second regions of substantially equal size including adjacent ones different in polarization direction from each other while letting each of the second regions be offset by a rotational angle from its corresponding one of the first regions of said first plat;
   wherein the first and second plates include a pair of first and second four-division type half-wave plates located at front and back positions of a light axis, each said half-wave plate has a surface divided into four regions by a couple of boundary lines crossing together at right angles, and a boundary line of the pair of first and second four-division type half-wave plates is offset by an angle of 45 degrees.

8. The apparatus of claim 7 wherein said first regions are the same in number as said second regions.

9. An apparatus for producing a multi-segmentally polarized light beam having rays differing in polarization state, comprising:
   a light source having an output for emission of a beam of linearly polarized light traveling along a principal axis;
   a first polarizing plate being situated in the principal axis of the light to oppose the output of said light source and having a surface segmented into a plurality of first regions of substantially equal size including adjacent ones being different in polarization direction from each other; and
   a second polarizing plate coaxially spaced apart from the first plate along the light axis, the second plate having its surface segmented into a plurality of second regions of substantially equal size including adjacent ones different in polarization direction from each other while letting each of the second regions be offset by a rotational angle from its corresponding one of the first regions of said first plate,
   wherein said first regions are the same in number as said second regions, and
   wherein the first and second plates include a pair of spaced-apart half-wave plates each having a round disc-like shape.

10. The apparatus of claim 9 wherein each of said first and second plates has a phase shift plane segmented into four substantially equal fan-like areas whereby the linearly polarized light beam as output from said light source is converted to a finally polarization-controlled light beam having eight differently polarized areas in its profile after penetration of said first and second plates.

11. The apparatus of claim 10 wherein the four fan-like areas of each of said first and second plates are substantially equally defined by a couple of boundary lines crossing together at right angles and wherein one of the boundary lines of said first plate is rotated by substantially forty-five (45) degrees from a corresponding boundary line of said second plate to thereby cause the eight polarized areas to be substantially equal in size.

12. The apparatus of claim 10 wherein the linearly polarized light has a first polarization direction and wherein the polarization-controlled light beam is set in a radially polarized state.

13. The apparatus of claim 10 wherein the linearly polarized light has a second polarization direction and wherein the polarization-controlled light beam is set in a azimuthally polarized state.

14. The apparatus of claim 9 wherein each of said first and second plates has a phase shift plane segmented into two semicircular areas whereby the linearly polarized light beam as output from said light source is converted to a finally polarization-controlled light beam having four different polarized areas in its profile after penetration of said first and second plates.

15. The apparatus of claim 14 wherein the two semicircular areas of each of said first and second plates are substantially equally defined by a boundary line and wherein the boundary lines of the first plate is rotated by substantially ninety (90) degrees from that of the second plate to thereby cause the four polarized areas to be substantially equal in size to one another.

16. The apparatus of claim 14 wherein the linearly polarized light has a first polarization direction and wherein the polarization-controlled light beam is set in a radially polarized state.

17. The apparatus of claim 14 wherein the linearly polarized light has a second polarization direction and wherein the polarization-controlled light beam is set in a azimuthally polarized state.

18. The apparatus of claim 9 further comprising:
   a rotatable half-wave plate placed between the output of said light source and said pair of spaced-apart half-wave plates, for causing the linearly polarized light beam leaving said light source to switch between first and second polarized states having first and second directions as offset by a prespecified angle from each other.

19. The apparatus of claim 18 wherein the prespecified angle is substantially ninety (90) degrees or angles polariscopically equivalent thereto.

20. The apparatus of claim 19 wherein the first polarization direction is substantially at right angles to an extending direction of a line segment contained in the light axis and perpendicular to the light axis whereas the second polarization direction is substantially identical to the direction of the line segment.

* * * * *